United States Patent

Hirota et al.

[11] 4,412,943
[45] Nov. 1, 1983

[54] LIQUID DETERGENT COMPOSITION

[75] Inventors: Hajime Hirota, Tokyo; Hiroshi Watanabe, Funabashi, both of Japan

[73] Assignee: Kao Soap Co., Ltd., Tokyo, Japan

[21] Appl. No.: 347,675

[22] Filed: Feb. 10, 1982

[30] Foreign Application Priority Data

Feb. 23, 1981 [JP] Japan .................................. 56-25257
Jan. 8, 1982 [JP] Japan .................................. 57-1604

[51] Int. Cl.³ .......................... C11D 1/38; C11D 3/26
[52] U.S. Cl. .................................. 252/546; 252/550; 252/551; 252/541; 252/142; 252/143; 252/DIG. 13; 252/DIG. 14
[58] Field of Search ............... 252/DIG. 14, DIG. 13, 252/550, 551, 541, 546, 559, 142, 143

[56] References Cited

U.S. PATENT DOCUMENTS

| | | | |
|---|---|---|---|
| 3,859,337 | 1/1975 | Herz et al. | 252/546 |
| 3,893,955 | 7/1975 | Hewitt et al. | 252/551 |
| 4,003,857 | 1/1977 | Gorsich et al. | 252/541 |
| 4,092,273 | 5/1978 | Inamorato et al. | 252/559 |
| 4,259,204 | 3/1981 | Homma | 252/DIG. 14 |
| 4,321,156 | 3/1982 | Bushman | 252/142 |

*Primary Examiner*—John E. Kittle
*Assistant Examiner*—Hoa Van Le
*Attorney, Agent, or Firm*—Flynn, Thiel, Boutell & Tanis

[57] ABSTRACT

A liquid detergent composition comprises:
(A) 5–25 wt. % of an ammonium alkyl sulfate of the formula (1):

$$R_1OSO_3NH_4 \tag{1}$$

wherein $R_1$ is a straight-chain or branched, saturated hydrocarbon group having 8–18 carbon atoms on the average, (B) 0.05–5 wt. % of an alkylenediaminecarboxylic acid derivative of the formula (2):

$$\begin{array}{c} A \\ \diagdown \\ B \end{array} N-R_2-N \begin{array}{c} C \\ \diagup \\ D \end{array} \tag{2}$$

wherein $R_2$ is an alkylene group having 2–3 carbon atoms, A, B, C and D may be the same or different and each is $$-R_3C(=O)-O-Y$$

or hydrogen, $R_3$ is $C_nH_{2n}$ (n being 1 or 2), or

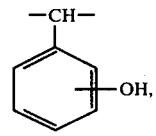

and Y is hydrogen or a cation, with the proviso that the number of hydrogen atoms contained in A, B, C and D is at most 2, and (C) 0.1 to 5 wt. % of a carboxylic acid, a salt of the carboxylic acid, an amino acid or a salt of the amino acid.

9 Claims, No Drawings

LIQUID DETERGENT COMPOSITION

The present invention relates to a liquid detergent composition. More particularly, the present invention relates to a liquid detergent composition having a suitable viscosity at the time of use, a low temperature gradient of viscosity and only a slight change with time.

The liquid detergent composition of the present invention may be used for various purposes. Particularly, it is used advantageously as a shampoo composition. The present invention will be described in detail mainly in this aspect.

As surfactants for shampoo compositions having a high foaming power, there may be mentioned ammonium alkyl sulfates. As compared with other surfactants such as polyoxyethylene alkyl ether sulfates, α-olefinsulfonates, 2-alkyl-N-carboxymethyl-N-carboxyethylimidazoliniumbetaine, nonyl phenyl ether and sulfate thereof, the above-mentioned surfactants have a high foaming power and afford a good finish after washing.

If a shampoo has an insufficient viscosity, it runs off from the palm of a user to make the handling thereof troublesome. Also for the purpose of enhancing the commercial value, the shampoo should have an increased viscosity. Generally, an inorganic salt, water-soluble high-molecular substance or higher fatty acid alkylolamide is used as a thickening agent. However, if a shampoo composition containing an ammonium alkyl sulfate as a base is thickened by an ordinary method, its viscosity at ambient temperature differs greatly from that at a low temperature and the shampoo has a quite unstable liquid state at the time of use after the storage. More particularly, if a shampoo has a suitable viscosity in summer, its viscosity is increased greatly in winter to make the flowing-out from a bottle difficult. On the other hand, if the shampoo has a suitable viscosity in winter, its viscosity becomes insufficient in summer and it runs off from the palm of a user to make the handling thereof troublesome and also to reduce the commercial value thereof.

After intensive investigations made for the purpose of overcoming the above defects while advantageous properties of the liquid detergent compositions containing an ammonium alkyl sulfate are sufficiently maintained, the inventors have found that, surprisingly, a liquid detergent composition exhibiting only a slight viscosity change with temperature, and also only insignificant coloring or pH change with time can be obtained by incorporating an alkylenediaminecarboxylic acid derivative and a carboxylic acid, an amino acid or a salt thereof in a shampoo composition containing an ammonium alkyl sulfate as the base. The present invention has been completed on the basis of this finding.

The present invention provides a liquid detergent composition characterized by containing:

(A) 5-25 wt. % of an ammonium alkyl sulfate of general formula (1):

$$R_1OSO_3NH_4 \tag{1}$$

wherein $R_1$ represents a straight-chain or branched, saturated hydrocarbon group having 8-18 carbon atoms in average, (B) 0.05-5 wt. % of an alkylenediaminecarboxylic acid derivative of the general formula (2):

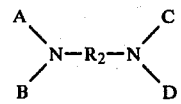

wherein $R_2$ represents an alkylene group having 2-3 carbon atoms, A, B, C and D may be the same or different and each represents

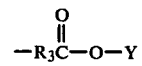

or hydrogen, $R_3$ represents $C_nH_{2n}$ (n being 1 or 2), or

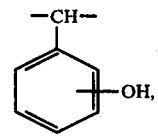

and Y represents hydrogen or a cation, with the proviso that the number of hydrogen atoms contained in A, B, C and D is at most 2, and (C) 0.1 to 5 wt. % of a carboxylic acid, a salt thereof, an amino acid or a salt thereof.

As the groups $R_1$ in the ammonium alkyl sulfates of general formula (1) used in the present invention, straight-chain or branched, saturated hydrocarbon groups having 10–14 carbon atoms on the average are highly preferred. The cation of Y in the formula (2) includes alkali metals such as sodium, potassium and lithium, alkaline earth metals such as calcium and magnesium, ammonium and alkanol ($C_1$–$C_3$) amines. Starting alcohols of those esters may be either natural or synthetic alcohols. The alcohols are esterified with sulfuric acid by an ordinary method and then neutralized with aqueous ammonia. Otherwise, the alcohols may be thermally reacted with sulfamic acid. As preferred alkylenediaminecarboxylic acid derivatives (B) represented by the above general formula (2), there may be mentioned ethylenediaminetetraacetate salts, ethylenediamine-N,N'-diacetate salts, ethylenediaminedi(o-hydroxyphenylacetate) salts and ethylenediamine-N,N'-dipropionate salts. The salts are those with alkali metals such as sodium, potassium and lithium, alkaline earth metals such as calcium and magnesium, ammonium and alkanolamines having 1-3 alkanol groups. The alkylenediaminecarboxylic acid derivatives may be used either alone or in the form of a mixture of two or more of them and incorporated in the liquid detergent composition in an amount of 0.05–5% (by weight; the same shall apply hereinafter), preferably 0.2–3%. If the amount is less than 0.05%, the coloring with time cannot be prevented. If the amount is more than 5%, on the other hand, the phase separation occurs at around 5° C.

As the carboxylic acids and salts thereof to be used as component C in the present invention, lower fatty acids, dicarboxylic acids, hydroxycarboxylic acids, unsaturated polybasic carboxylic acids and their salts are preferred.

The lower fatty acids are those having 1 to 8 carbon atoms. They include formic acid, acetic acid, propionic acid, butyric acid, valeric acid and caproic acid. As the dicarboxylic acid, there may be mentioned those having 2 to 7 carbon atoms such as oxalic acid, malonic acid, succinic acid, glutaric acid, adipic acid and pimelic acid. As the hydroxycarboxylic acids, there may be mentioned, for example, glycolic acid, lactic acid, hydroacrylic acid, α- or β-hydroxybutyric acid, glyceric acid, tartronic acid, malic acid, tartaric acid and citric acid. As the unsaturated polybasic carboxylic acids, there may be mentioned, for example, maleic acid, fumaric acid, mesaconic acid and citraconic acid.

Among the above acids, malonic acid, succinic acid, lactic acid, tartaric acid, citric acid and their salts are preferred. As the salts, there may be mentioned alkali metal salts, alkaline earth metal salts, ammonium salts and salts with alkanolamines having 1-3 alkanol groups having 2 or 3 carbon atoms.

The amino acid to be used as the component (C) includes neutral amino acids, acidic amino acids, basic amino acids, oxyamino acids, imino acids, sulfur-containing amino acids and the like. As the neutral amino acids, there are glycine, alanine, valine, leucine, isoleucine, phenylalanine, tryptophane, sarcosine, β-alanine, γ-aminobutyric acid, ε-aminocaproic acid. As the acidic amino acids, there are glutamic acid, aspartic acid, cysteic acid and homocysteic acid. As the basic acids, there are lysine, ornithine, arginine. As the oxyamino acids, there are serine, homoserine, tryosine and threonine. As the imino acids, there are proline and hydroxyproline. As the sulfur-containing amino acids, there are cystine, cysteine and methionine. Any optical isomer of the above listed compounds may be used in the invention. The neutral amino acids and acidic amino acids are preferable and the neutral amino acids are most preferable. As stated above, these amino acids may be used in the form of either the acid or a salt thereof. The salt of an amino acid includes salts of alkali metals such as sodium, potassium and lithium, salts of alkaline earth metals such as calcium and magnesium, ammonium salts, salts containing one the three alkanolamines having 2 or 3 carbon atoms, and salts of basic amino acids such as lysine, arginine and ornithine. The alkali metal salt of an amino acid is most preferable.

The component (C), acid or a salt thereof, may be used either alone or in the form of a mixture of two or more of them and incorporated in the liquid detergent composition in an amount of 0.1-5 wt. %, preferably 0.2-3 wt. %. If the amount is less than 0.1%, the intended effects cannot be obtained, while on the other hand, if the amount is more than 5%, the phase separation occurs.

The liquid detergent composition of the present invention may contain other components (for example, other known components of shampoo in case it is used as a shampoo composition) in addition to the above three indispensable components.

There may be incorporated in the detergent composition of the present invention amphoteric surfactants, nonionic surfactants, solubilizers such as propylene glycol, glycerin or urea, viscosity modifiers such as ethyl alcohol, isopropyl alcohol, hydroxyethylcellulose, methylcellulose or higher alcohols, perfumes, dyes, U.V. absorbers, antioxidants, antiseptics and appearance-modifying agents (such as pearlescent pigment) in an amount which does not deteriorate the effects of the present invention, if necessary.

The liquid detergent composition of the present invention can be used in a broad pH range of from weakly acidic to weakly alkaline pH, a pH value of 4 to 10.

The following examples will further illustrate the present invention, which by no means limit the present invention.

Test methods in the following examples were as follows:

(1) Viscosity measuring method:

300 g of a sample was charged in a 300 ml beaker and its viscosities at liquid temperatures of 30° C. and 5° C. were measured by means of a BM type viscometer (a product of Tokyo Keiki Co.).

(2) High-temperature stability:

(a) Coloring:

A sample in a transparent vessel was stored in a constant temperature bath at 50° C. for one month and the coloring was judged macroscopically.

Macroscopic judgement of coloring:

o: The sample was scarcely colored.

x: The sample was colored.

(b) pH change:

A sample having a given, controlled pH was stored in a constant temperature bath at 50° C. for one month and its pH was measured again after the storage.

(3) Liquid condition at low temperature:

A sample was charged in a 100 ml transparent glass vessel. The vessel was tightly closed and stored in a constant temperature bath at 5° C. for one month. Change in condition of the sample was observed macroscopically.

o: The sample was homogeneous and transparent.

x: The phase separation or solidification was observed.

EXAMPLE 1

A shampoo composition containing ammonium lauryl sulfate prepared from a natural alcohol having 12 carbon atoms on the average as the main component was prepared according to the following recipe and its effects were examined. The results are shown in Table 1.

| Composition: | |
|---|---|
| Ammonium lauryl sulfate | 14.0% |
| Lauric acid diethanolamide | 3.0% |
| Disodium ethylenediaminetetraacetate | see Table 1 |
| Carboxylic acid salt | |
| pH regulator (sulfuric acid or potassium hydroxide) | Suitable amount |
| Water | Balance |

TABLE 1

| | Composition No. | | | | | | | | | |
|---|---|---|---|---|---|---|---|---|---|---|
| | Comparative | | Present Invention | | | | | | | Comparative |
| | 1 | 2 | 3 | 4 | 5 | 6 | 7 | 8 | 9 | 10 |
| Disodium ethyleneaminetetraacetate (%) | 0 | 0.3 | 0.3 | 0.3 | 0.3 | 0.3 | 0.3 | 0.3 | 0.3 | — |
| Monosodium malonate (%) | 0 | | 0.8 | | | | | | | |
| Diammonium succinate (%) | 0 | | | 0.5 | | | | | | 0.2 |
| Potassium lactate (%) | 0 | | | | 0.4 | | | | | |

TABLE 1-continued

|  | Composition No. | | | | | | | | | |
|---|---|---|---|---|---|---|---|---|---|---|
|  | Comparative | | Present Invention | | | | | | | Comparative |
|  | 1 | 2 | 3 | 4 | 5 | 6 | 7 | 8 | 9 | 10 |
| Monosodium tartrate (%) | 0 |  |  |  |  | 0.7 |  |  |  |  |
| Trisodium citrate (%) | 0 |  |  |  |  |  | 0.3 |  |  |  |
| Potassium formate (%) | 0 |  |  |  |  |  |  | 0.4 |  |  |
| Monoammonium maleate (%) | 0 |  |  |  |  |  |  |  | 0.5 |  |
| Viscosity at 30° C. (cp) | 314 | 325 | 406 | 348 | 332 | 354 | 365 | 321 | 342 | 318 |
| Viscosity at 5° C. (cp) | 9,628 | 8,430 | 821 | 842 | 764 | 810 | 822 | 884 | 876 | 8,390 |
| Initial pH* | 7.0 | 7.0 | 5.0 | 6.0 | 7.0 | 5.5 | 6.0 | 7.5 | 5.0 | 7.0 |
| pH after storage at high temp. | 8.7 | 7.3 | 4.9 | 6.1 | 7.1 | 5.5 | 6.1 | 7.6 | 4.9 | 8.6 |
| Coloring after storage at high temp. | x | x | o | o | o | o | o | o | o | x |

*Finely controlled with sulfuric acid or sodium hydroxide

EXAMPLE 2

Results of tests on amounts of the three indispensable components are shown in Table 2.

TABLE 2

| Composition No. | Present Invention | | | | | | Comparative | | | |
|---|---|---|---|---|---|---|---|---|---|---|
|  | 11 | 12 | 13 | 14 | 15 | 16 | 17 | 18 | 19 | 20 |
| Ammonium lauryl sulfate (%) | 15 | 15 | 15 | 15 | 15 | 15 | 15 | 15 | 15 | 15 |
| Monopotassium ethylenediamine-N,N'—diacetate (%) | 1.0 |  |  |  |  |  | 0.02 | 5.2 |  |  |
| Trisodium ethylenediamine-tetraacetate (%) |  | 1.4 |  |  |  |  |  | 0.3 |  | 0.3 |
| Monopotassium ethylenediamine-di(hydroxyphenylacetate) (%) |  |  | 0.8 |  |  |  |  |  |  |  |
| Monoammonium ethylenediamine-N,N'—dipropionate (%) |  |  |  | 0.6 |  |  |  |  |  | 0.4 |
| Diammonium propylenediamine-tetraacetate (%) |  |  |  |  | 1.6 |  |  |  |  |  |
| Tartaric acid (%) | 0.5 | 0.5 | 0.5 | 0.5 | 0.5 | 2.5 | 0.5 | 0.5 | 0.05 | 5.1 |
| Water | Balance | | | | | | | | | |
| Viscosity at 30° C. (cp) | 212 | 220 | 208 | 200 | 234 | 248 | 208 | 268 | 174 | 308 |
| Viscosity at 5° C. (cp) | 564 | 534 | 544 | 518 | 528 | 572 | 4,728 | 688 | 4,024 | 742 |
| Initial pH* | 5.0 | 7.0 | 7.0 | 6.0 | 7.0 | 5.0 | 7.0 | 5.0 | 7.0 | 5.0 |
| pH after storage at high temp. (one month) | 5.1 | 7.1 | 7.1 | 6.2 | 7.0 | 5.0 | 7.8 | 5.1 | 7.9 | 5.1 |
| Coloring after storage at high temp. (one month) | o | o | o | o | o | o | x | o | x | o |
| Liquid condition at low temp. | o | o | o | o | o | o | o | x | o | x |

*Finely controlled with sulfuric acid or sodium hydroxide

EXAMPLE 3

Shampoo compositions as shown in Table 3-6 were prepared and their effects were examined. The results are shown in Tables 3-6.

TABLE 3

| Composition No. | 21 | 22 | 23 |
|---|---|---|---|
| Ammonium lauryl sulfate | 15.0% | 15.0% | 15.0% |
| Ammonium chloride | 0.5 | 0.5 | 0.5 |
| Disodium ethylenediamine-tetraacetate | 1.0 | — | 1.0 |
| Succinic acid | 0.3 | 0.3 | — |
| Perfume | 0.3 | 0.3 | 0.3 |
| Dye | trace amount | trace amount | trace amount |
| Water | balance | balance | balance |
| pH* | 5.2 | 5.2 | 5.2 |
| Viscosity at 30° C. (cp) | 812 | 785 | 774 |
| Viscosity at 5° C. (cp) | 1,624 | 11,200 | 10,214 |

*Sulfuric acid or sodium hydroxide was used for the fine control of pH.

TABLE 4

| Composition No. | 24 | 25 | 26 |
|---|---|---|---|
| Ammonium lauryl sulfate | 14.0% | 14.0% | 14.0% |
| Lauric acid diethanolamide | 5.0 | 5.0 | 5.0 |
| Monoammonium ethylene-diamine-N,N'—dipropionate | 0.5 | — | 0.5 |
| Citric acid | 0.4 | 0.4 | — |
| Ethylene glycol distearate | 2.0 | 2.0 | 2.0 |
| Perfume | 0.3 | 0.3 | 0.3 |
| Dye | trace amount | trace amount | trace amount |
| Water | balance | balance | balance |
| pH* | 5.5 | 5.5 | 5.5 |
| Viscosity at 30° C. (cp) | 1,200 | 1,164 | 1,108 |
| Viscosity at 5° C. (cp) | 2,647 | 36,242 | 33,424 |

*Sulfuric acid or sodium hydroxide was used for the fine control of pH.

TABLE 5

| Composition No. | 27 | 28 | 29 |
|---|---|---|---|
| Ammonium lauryl sulfate | 13.0% | 13.0% | 13.0% |
| Methylcellulose** | 1.0 | 1.0 | 1.0 |
| Monosodium ethylene-diamine-N,N'—diacetate | 0.8 | — | 0.8 |
| Malonic acid | 0.6 | 0.6 | — |
| Perfume | 0.3 | 0.3 | 0.3 |
| Dye | trace amount | trace amount | trace amount |
| Water | balance | balance | balance |
| pH* | 6.0 | 6.0 | 6.0 |
| Viscosity at 30° C. (cp) | 1,054 | 1,084 | 1,112 |

TABLE 5-continued

| Composition No. | 27 | 28 | 29 |
|---|---|---|---|
| Viscosity at 5° C. (cp) | 2,180 | 21,214 | 25,324 |

*Sulfuric acid or sodium hydroxide was used for the fine control of pH.
**Methylcellulose used had a viscosity of 5,000 cp in 2% aqueous solution.

TABLE 6

| Composition No. | 30 | 31 | 32 |
|---|---|---|---|
| Ammonium lauryl sulfate | 17% | — | — |
| Sodium lauryl sulfate | — | 17 | — |
| Triethanolamine salt of lauryl sulfate | — | — | 17 |
| Lactic acid | 0.6 | 0.6 | 0.6 |
| Trisodium ethylene-diaminetetraacetate | 0.2 | 0.2 | 0.2 |
| Perfume | 0.3 | 0.3 | 0.3 |
| Dye | trace amount | trace amount | trace amount |
| Water | balance | balance | balance |
| pH* | 6.5 | 6.5 | 6.5 |
| Viscosity at 30° C. (cp) | 724 | 204 | 54 |
| Viscosity at 5° C. (cp) | 1,214 | solidified | 424 |

*Sulfuric acid or sodium hydroxide was used for the fine control of pH.

The composition containing sodium lauryl sulfate was crystallized at 5° C. The composition containing triethanolamine salt of lauryl sulfate could not be thickened and it readily ran off from the palm at the time of the use and it could not be used easily.

EXAMPLE 4

A shampoo composition containing ammonium lauryl sulfate prepared from a natural alcohol having 12 carbon atoms on the average as the main component was prepared according to the following recipe and its effects were examined. The results are shown in Table 7.

| Composition: | |
|---|---|
| Ammonium lauryl sulfate having the carbon number of 12 on the average | 15.0% |
| Coconut fatty acid diethanolamide having the carbon number of 12 on the average | 4.0% |
| Disodium ethylenediamine-tetraacetate | see Table 7 |
| Amino acid or a salt thereof | |
| pH regulator (sulfuric acid or potassium hydroxide) | Suitable amount |
| Water | Balance |

TABLE 7

| | Control | | The Invention | | | | | | | Control |
|---|---|---|---|---|---|---|---|---|---|---|
| Composition No. | 33 | 34 | 35 | 36 | 37 | 38 | 39 | 40 | 41 | 42 |
| Disodium ethyleneamine-tetraacetate (%) | 0 | 0.2 | 0.2 | 0.2 | 0.2 | 0.2 | 0.2 | 0.2 | 0.2 | 0 |
| Glycine (%) | 0 | 0 | 0.4 | | | | | | | 0.2 |
| Sodium glycine (%) | 0 | 0 | | 0.6 | | | | | | |
| L-alanine (%) | 0 | 0 | | | 0.5 | | | | | |
| Sodium L-valine (%) | 0 | 0 | | | | 0.7 | | | | |
| Phenylalanine (%) | 0 | 0 | | | | | 0.8 | | | |
| Sarcosine (%) | 0 | 0 | | | | | | 0.3 | | |
| Ammonium ε-aminocaproate (%) | 0 | 0 | | | | | | | 0.5 | |
| Viscosity at 30° C. (cp) | 532 | 540 | 572 | 530 | 564 | 610 | 583 | 538 | 565 | 524 |
| Viscosity at 5° C. (cp) | 12,340 | 9,820 | 940 | 890 | 920 | 1,120 | 924 | 894 | 948 | 7,250 |
| Initial pH | 7.0 | 7.0 | 5.5 | 7.0 | 6.0 | 5.8 | 7.0 | 5.7 | 7.5 | 5.5 |
| pH after storage at high temp. | 8.7 | 7.4 | 5.4 | 7.0 | 6.1 | 5.8 | 7.1 | 5.8 | 7.5 | 6.0 |
| Coloring after storage at high temp. | x | x | o | o | o | o | o | o | o | x |

EXAMPLE 5

Results of tests on amounts of the three indispensable components are shown in Table 8.

TABLE 8

| | Present Invention | | | | | | Comparative | | | |
|---|---|---|---|---|---|---|---|---|---|---|
| Composition No. | 43 | 44 | 45 | 46 | 47 | 48 | 49 | 50 | 51 | 52 |
| Ammonium lauryl sulfate (%) | 15 | 15 | 15 | 15 | 15 | 15 | 15 | 15 | 15 | 15 |
| Monopotassium salt of ethylene diamine-N,N'—diacetic acid (%) | 0.5 | | | | | 0.1 | | | | |
| Trisodium salt of ethylene diamine tetraacetic acid (%) | | 0.1 | | | | | 0.02 | | 0.3 | |
| Monopotassium salt of ethylene diamine-di(hydroxyphenyl-acetic acid) (%) | | | 0.3 | | | | | 5.3 | | |
| Monoammonium salt of ethylene diamine-N,N'—dipropionic acid (%) | | | | 0.7 | | | | | | |
| Diammonium salt of propylene diamine tetraacetic acid (%) | | | | | 0.8 | | | | | 0.4 |
| Sarcosine (%) | 0.5 | 0.5 | 1.0 | 0.5 | 0.3 | 3.0 | 0.5 | 0.5 | 0.05 | 5.5 |
| Water | | | | Balance | | | | | | |
| Viscosity at 30° C. (cp) | 210 | 234 | 243 | 220 | 245 | 284 | 216 | 284 | 180 | 321 |
| Viscosity at 5° C. (cp) | 560 | 566 | 575 | 557 | 583 | 623 | 4,290 | 633 | 4,120 | 733 |
| Initial pH | 5.0 | 7.5 | 5.5 | 6.0 | 7.0 | 5.5 | 7.0 | 5.5 | 7.0 | 5.7 |
| pH after storage at high temp. (one month) | 5.0 | 7.6 | 5.6 | 6.1 | 7.0 | 5.6 | 7.8 | 5.5 | 7.7 | 5.7 |
| Coloring after storage | o | o | o | o | o | o | x | o | x | o |

TABLE 8-continued

|  | Present Invention | | | | | | Comparative | | | |
|---|---|---|---|---|---|---|---|---|---|---|
| Composition No. | 43 | 44 | 45 | 46 | 47 | 48 | 49 | 50 | 51 | 52 |
| at high temp. (one month) | | | | | | | | | | |
| Liquid condition at low temp. | o | o | o | o | o | o | o | x | o | x |

EXAMPLE 6

Shampoo compositions as shown in Tables 9–12 were prepared and their effects were examined. The results are shown in Tables 9–12.

TABLE 9

| (transparent shampoo of a low viscosity) | | | |
|---|---|---|---|
| Composition No. | 53 | 54 | 55 |
| Ammonium lauryl sulfate | 14.0% | 14.0% | 14.0% |
| Ammonium chloride | 0.3 | 0.3 | 0.3 |
| Disodium ethylenediamine-tetraacetate | 0.5 | — | 0.5 |
| Phenylalanine | 0.5 | 0.5 | — |
| Perfume | 0.3 | 0.3 | 0.3 |
| Dye | trace amount | trace amount | trace amount |
| Water | balance | balance | balance |
| pH* | 5.5 | 5.5 | 5.5 |
| Viscosity at 30° C. (cp) | 340 | 308 | 295 |
| Viscosity at 5° C. (cp) | 724 | 6,250 | 5,940 |

*Sulfuric acid or sodium hydroxide was used for the fine control of pH.

It is noted that Nos. 54 and 55 have a remarkably increased viscosity at a low temperature.

TABLE 10

| (pearl-like shampoo) | | | |
|---|---|---|---|
| Composition No. | 56 | 57 | 58 |
| Ammonium lauryl sulfate | 15.0% | 15.0% | 15.0% |
| Coconut fatty acid monoethanolamide | 3.0 | 3.0 | 3.0 |
| Monopotassium ethylene-diamine-N,N'—diacetate | 0.8 | — | 0.8 |
| ε-amino caproic acid | 0.4 | 0.4 | — |
| Ethylene glycol distearate | 1.5 | 1.5 | 1.5 |
| Perfume | 0.3 | 0.3 | 0.3 |
| Dye | trace amount | trace amount | trace amount |
| Water | balance | balance | balance |
| pH* | 5.8 | 5.8 | 5.8 |
| Viscosity at 30° C. (cp) | 1,320 | 1,124 | 1,210 |
| Viscosity at 5° C. (cp) | 2,836 | 29,320 | 31,524 |

*Sulfuric acid or sodium hydroxide was used for the fine control of pH.

It is noted that Nos. 57 and 58 have only a low flowability at 5° C. and eventually is difficult to flow out of a container.

TABLE 11

| (transparent shampoo of a high viscosity) | | | |
|---|---|---|---|
| Composition No. | 59 | 60 | 61 |
| Ammonium lauryl sulfate | 16.0% | 16.0% | 16.0% |
| Methylcellulose** | 1.2 | 1.2 | 1.2 |
| Monosodium ethylenediamine-N,N'—dipropionic acid | 0.6 | — | 0.6 |
| Sodium glycine | 0.8 | 0.8 | — |
| Perfume | 0.3 | 0.3 | 0.3 |
| Dye | trace amount | trace amount | trace amount |
| Water | balance | balance | balance |
| pH* | 6.5 | 6.5 | 6.5 |
| Viscosity at 30° C. (cp) | 1,560 | 1,480 | 1,630 |
| Viscosity at 5° C. (cp) | 2,640 | 18,350 | 20,130 |

*Sulfuric acid or sodium hydroxide was used for the fine control of pH.
**Methylcellulose used had a viscosity of 5,000 cp in 2% aqueous solution It is noted that Nos. 60 and 61 are not stable in respect to the liquid state.

TABLE 12

| (lauryl sulfate contained in shampoo is different in counter ion) | | | |
|---|---|---|---|
| Composition No. | 62 | 63 | 64 |
| Ammonium lauryl sulfate | 18.0% | — | — |
| Sodium lauryl sulfate | — | 18.0 | — |
| Triethanolamine salt of lauryl sulfate | — | — | 18.0 |
| Sarcosine | 0.5 | 0.5 | 0.5 |
| Trisodium ethylenediamine-tetraacetate | 0.4 | 0.4 | 0.4 |
| Perfume | 0.3 | 0.3 | 0.3 |
| Dye | trace amount | trace amount | trace amount |
| Water | balance | balance | balance |
| pH* | 7.0 | 7.0 | 7.0 |
| Viscosity at 30° C. (cp) | 890 | 1,030 | 68 |
| Viscosity at 5° C. (cp) | 1,380 | solidified | 430 |

*Sulfuric acid or sodium hydroxide was used for the fine control of pH.

The composition containing sodium lauryl sulfate was crystallized at 5° C. The composition containing triethanolamine salt of lauryl sulfate could not be thickened and it readily ran off from the palm at the time of the use and it could not be used easily.

The embodiments of the invention in which an exclusive property or privilege is claimed are defined as follows:

1. A liquid detergent composition which consists essentially of:
(A) from 5 to 25 wt. % of an ammonium alkyl sulfate having the formula

$$R_1OSO_3NH_4$$

wherein $R_1$ is alkyl having from 8 to 18 carbon atoms on the average,
(B) from 0.05 to 5 wt. % of one or a mixture of two or more alkylenediaminecarboxylic acid derivatives having the formula

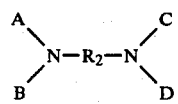

wherein $R_2$ is alkylene having 2 or 3 carbon atoms; A, B, C and D, which are the same or different, each is

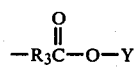

or hydrogen, in which $R_3$ is $—C_nH_{2n}—$ or

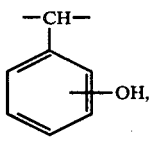

n is 1 or 2 and Y is hydrogen or a cation, with the proviso that from 0 to 2 of the groups, A, B, C and D are hydrogen and the remainder are

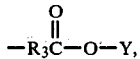

(C) from 0.1 to 5 wt. % of one or a mixture of two or more compounds selected from the group consisting of carboxylic acids selected from the group consisting of lower fatty acids having from 1 to 8 carbon atoms, dicarboxylic acids having the formula HOOC–(CH$_2$)$_n$COOH wherein n is an integer of from 0 to 5, glycolic acid, lactic acid, hydroacrylic acid, α-hydroxybutyric acid, β-hydroxybutyric acid, glyceric acid, tartronic acid, malic acid, tartaric acid, citric acid, maleic acid, fumaric acid, mesaconic acid and citraconic acid, and amino acids selected from the group consisting of glycine, alanine, valine, leucine, isoleucine, phenylalanine, tryptophane, sarcosine, β-alanine, γ-aminobutyric acid, ε-aminocaproic acid, glutamic acid, aspartic acid, cysteic acid, homocysteic acid, lysine, ornithine, arginine, serine, homoserine, tyrosine, threonine, proline, hydroxyproline, cystine, cysteine and methionine, and salts of said carboxylic acids and said amino acids, and (D) the balance is essentially water.

2. A composition as claimed in claim 1 in which R$_1$ is alkyl having 10 to 14 carbon atoms.

3. A composition as claimed in claim 2 in which said alkylenediaminecarboxylic acid derivative is selected from the group consisting of ethylenediaminetetraacetate salts, ethylenediamine-N,N'-diacetate salts, ethylenediamine di(O-hydroxyphenylacetate) salts and ethylenediamine-N,N'-dipropionate salts.

4. A composition as claimed in claim 3 in which the amount of said alkylenediaminecarboxylic acid derivative is from 0.2 to 3 wt. %.

5. A liquid detergent composition as claimed in claim 1 wherein the component (C) is selected from the group consisting of lower fatty acids having from 1 to 8 carbon atoms, dicarboxylic acids having the formula HOOC–(CH$_2$)$_n$COOH wherein n is an integer of from 0 to 5, glycolic acid, lactic acid, hydroacrylic acid, α-hydroxybutyric acid, β-hydroxybutyric acid, glyceric acid, tartronic acid, malic acid, tartaric acid, citric acid, maleic acid, fumaric acid, mesaconic acid and citraconic acid, and salts thereof.

6. A liquid detergent composition as claimed in claim 1 wherein the component (C) is selected from the group consisting of glycine, alanine, valine, leucine, isoleucine, phenylalanine, tryptophane, sarcosine, β-alanine, γ-aminobutyric acid, ε-aminocaproic acid, glutamic acid, aspartic acid, cysteic acid, homocysteic acid, lysine, ornithine, arginine, serine, homoserine, tyrosine, threonine, proline, hydroxyproline, cystine, cysteine and methionine, and salts thereof.

7. A composition as claimed in claim 3 in which (C) is an amino acid selected from the group consisting of glycine, alanine, valine, leucine, isoleucine, phenylalanine, tryptophane, sarcosine, β-alanine, γ-aminobutyric acid and ε-aminocaproic acid.

8. A composition as claimed in claim 4, in which the amount of said amino acid is from 0.2 to 3 wt. %.

9. A composition as claimed in claim 3 wherein component (C) is selected from the group consisting of malonic acid, succinic acid, lactic acid, tartaric acid, citric acid, alkali metal salts of said acids, alkaline earth metal salts of said acids, ammonium salts of said acids and alkanolamine salts of said acids.

* * * * *